United States Patent [19]
Snead

[11] Patent Number: 5,662,601
[45] Date of Patent: Sep. 2, 1997

[54] SUPPOSITORY APPLICATOR

[76] Inventor: Patty B. Snead, 2911 10th Ave. South, Birmingham, Ala. 35205-1001

[21] Appl. No.: 569,494

[22] Filed: Dec. 8, 1995

[51] Int. Cl.$^6$ .............................. A61F 13/20; A61M 5/00; A61M 31/00
[52] U.S. Cl. ................ 604/15; 604/57; 604/117; 604/285
[58] Field of Search .................. 604/11–19, 48, 604/57–60, 93, 174, 275–278, 285, 288, 117

[56] References Cited

U.S. PATENT DOCUMENTS

| | | | |
|---|---|---|---|
| D. 330,764 | 11/1992 | Lorentzon | D24/141 |
| 939,693 | 11/1909 | Holtzmann | 604/60 |
| 2,047,437 | 7/1936 | Sinkler | 604/60 |
| 2,754,822 | 7/1956 | Emelock | 604/59 |
| 3,297,031 | 1/1967 | Bray | 604/59 |
| 3,842,834 | 10/1974 | Vass | 128/245 |
| 3,906,948 | 9/1975 | Vass | 128/245 |
| 4,060,083 | 11/1977 | Hanson | 604/59 |
| 4,990,136 | 2/1991 | Geria | 604/63 |
| 5,330,427 | 7/1994 | Weissenburger | 604/14 |

FOREIGN PATENT DOCUMENTS

| | | |
|---|---|---|
| 1165850 | 10/1958 | France . |
| 1286634 | 1/1962 | France . |

*Primary Examiner*—David H. Willse
*Assistant Examiner*—David J. Cho
*Attorney, Agent, or Firm*—John D. Gougliotta; David L. Volk

[57] ABSTRACT

A suppository applicator is disclosed having a cylindrical, hollow barrel forming a suppository chamber at one end, and guiding a plunger shaft at the other end. The plunger shaft terminates at a plunger head which slidably travels within the suppository chamber. A stop shield is formed annularly about and extending outward from the barrel, and forms both an insertion as well as a shield. A grippable lip opposed to the gripping portion of the plunger shaft is also included.

7 Claims, 1 Drawing Sheet

SUPPOSITORY APPLICATOR

BACKGROUND OF THE INVENTION

1. Field of the Invention

The present invention relates generally to a suppository applicator for applying medications to a rectal body cavity, and, more particularly, to a suppository applicator incorporating a stopping shield to aid in the proper insertion of the device.

2. Description of the Related Art

In the related art, many suppository applicators are known. For example, in U.S. Pat. No. 5,330,427, issued in the name of Weissenburger, discloses a prefilled suppository applicator having a flexible chamber which is inverted during use in order to expel medication from the applicator. Such a pre-filled applicator would necessarily only accommodate a single use, and require refrigeration in order to prevent premature melting of the contents. Such a refrigerated applicator could cause significant discomfort.

Also, in U.S. Pat. No. 4,990,136, issued in the name of Geria, a suppository applicator is disclosed which holds a suppository at a tip and expels the suppository with a spring tensioned plunger. Should such a complex mechanism malfunction, injury to the rectal cavity could result.

And again, in U.S. Pat. No. 3,906,948, issued in the name of Vass, a rectal applicator for administering enemas is disclosed including a plate-like enlargement which allows an applicator nozzle to be administered centrally within anal canal, especially when treating infants or small children. Such a device appear unadaptable for use in holding or ejecting a suppository.

Similarly, in U.S. Pat. No. 3,842,834, issued in the name of Vass, an adjustable rectal applicator with fluid distributing and draining nozzle is disclosed which also uses a similar plate-like enlargement in conjunction with a unique, bulbous nozzle head in order to administer to and drain fluids from the rectal cavity. Once again, such a device appear unadaptable for use in holding or ejecting a suppository.

And finally, in U.S. Pat. No. Des. 330,764, issued in the name of Lorentzon, an ornamental design for a rectal applicator for pharmaceutical products is shown.

Although many if these references disclose devices that can aid in the application of suppositories into a body cavity, none provide the ease and convenience of plunger aided insertion in combination with increased sanitary conditions as well as error-free convenience associated with an integrated stop shield. Consequently, a need has been felt for providing an apparatus which combines such features.

SUMMARY OF THE INVENTION

It is therefore an object of the present invention to provide an improved suppository applicator.

It is yet another object of the present invention to provide an improved suppository applicator having a suppository chamber which prevents premature melting of the suppository prior to complete insertion.

It is yet another object of the present invention to provide an improved suppository applicator having a plunger to aid in the control of the insertion of suppositories.

It is yet another object of the present invention to provide an improved suppository applicator having a grippable lip to aid the user in thrusting a plunger when utilizing the applicator in uncomfortable or inconvenient orientations.

It is a final object of the present invention to provide an improved suppository applicator having a stop shield to allow a user a sanitary and effective manner of introducing the applicator to an effective, pre-determined insertion depth.

It is a feature of the present invention to provide an improved suppository applicator having an integral stop shield formed annularly about and extending outward from a hollow barrel which holds a suppository.

Briefly described according to one embodiment of the present invention, a suppository applicator is disclosed having a cylindrical, hollow barrel forming a suppository chamber at one end, and guiding a plunger shaft at the other end. The plunger shaft terminates at a plunger head which slidably travels within the suppository chamber in order to urge outward any suppository within the chamber. A stop shield is formed annularly about and extending outward from the barrel, and forms both an insertion stop to aid in the proper insertion of the barrel, as well as a shield to provide sanitary protection of one's hands. A grippable lip opposed to the gripping portion of the plunger shaft is also included to aid the user in thrusting a plunger when utilizing the applicator in uncomfortable or inconvenient orientations.

An advantage of the present invention is that a suppository chamber prevents the premature melting of the suppository prior to complete insertion.

Another advantage of the present invention is that a plunger aids in the control of the insertion of suppositories quick, effective insertion of suppositories.

Yet another advantage of the present invention is that a grippable lip is provided to aid the user in thrusting a plunger when utilizing the applicator in uncomfortable or inconvenient orientations.

Finally, the present invention provides a stop shield to allow a user a sanitary and effective manner of introducing the applicator to an effective, predetermined insertion depth.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

1. Detailed Description of the Figures

Figure 1:
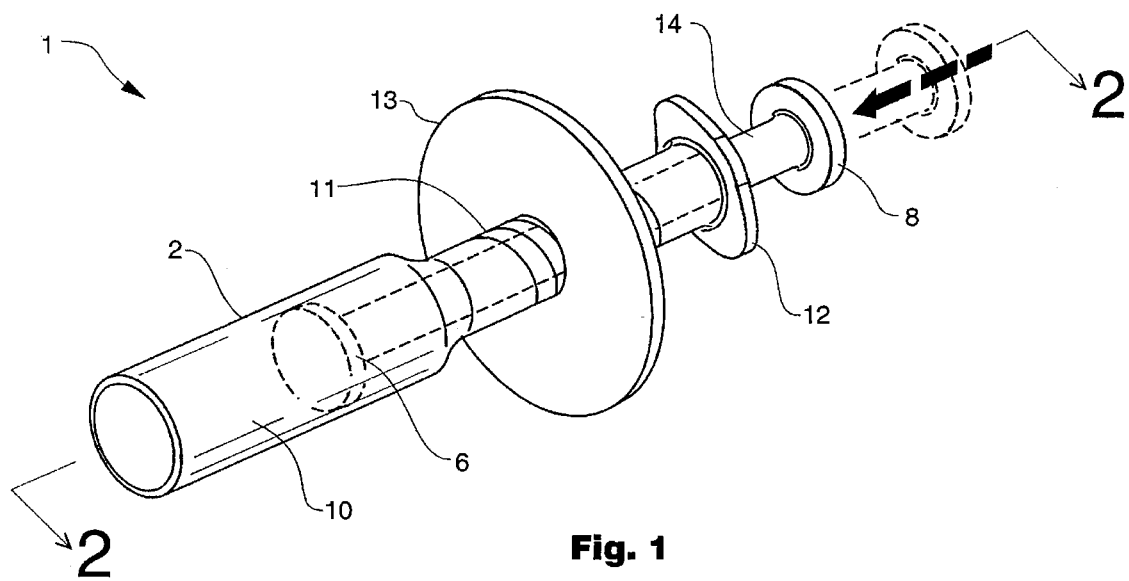
FIG. 1 is a perspective view of the preferred embodiment of the present invention.
Figure 2:
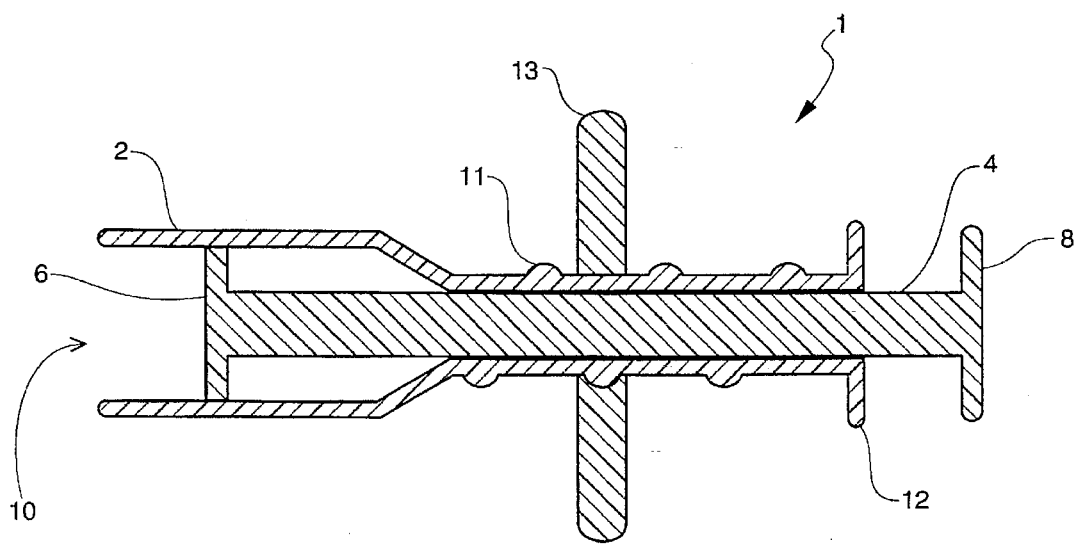
FIG. 2 is a cross sectional view thereof taken along lines II-II of FIG. 1.

Referring now to the figures, a suppository applicator, generally noted as 1, is shown, according to the present invention, having a generally cylindrical, hollow barrel 2. Within the barrel 2 is slidably retained a plunger shaft 4. The plunger shaft 4 terminates at the internal end in a plunger head 6, and at the external end in a plunger handle 8. The frontmost portion of the barrel 2 forms a suppository holding chamber 10. The rearmost portion of the barrel 2 forms a grippable lip 12. In its preferred embodiment, the exterior portion of the barrel 2 contains adjustment threads 11, and supports a stop shield 13 which is guided upon the threads 11 in a manner such that horizontal location of the stop shield 13 can be adjusted simply by twisting the stop shield 13 and the barrel 2 relative to each other. It is also envisioned that the stop shield 13 can be pressed tightly against the barrel 2, in order to provide a slide adjustment means not requiring threads 11. It is also currently envisioned that a stop shield 13 can be formed in a fixed position extending annularly outward from a location near the middle of the barrel 2 in order to produce a non-adjustable version.

As opposed to the related art cited above, in its preferred embodiment it is currently envisioned that the present invention can be easily and inexpensively manufactured as two or three pieces of injected molded plastic, thereby easily become available for either reusable or disposable use. It is also envisioned that the present invention can be manufactured in different sizes, thereby easily accommodating a wide range of adults and infants.

2. Operation of the Preferred Embodiment

In operation, the present invention is easily utilized in one particular procedure by placing a suppository within the suppository holding chamber 10. The walls of the holding chamber 10 prevent immediate contact with the body, thereby preventing the suppository from melting prematurely. The stop shield 13 is then adjusted according to the size of the individual. The applicator 1 can then be inserted within a rectal body cavity, and the plunger handle 8 moved forward to urge the contents of the suppository holding chamber 10 forward. Plunger movement is easily achieved by placing one's fingers grippingly around the grippable lip 12 and one's thumb upon the plunger handle 8, then squeezing slowly.

The applicator can then be disposed, or cleaned and re-used. The plunger 4 can be retracted, and the stop shield 13 can be readjusted to better accommodate the individual, if necessary.

The foregoing description is included to illustrate the operation of the preferred embodiment and is not meant to limit the scope of the invention. The scope of the invention is to be limited only by the following claims.

What is claimed is:

1. A suppository applicator comprising:

a cylindrical barrel, said barrel being hollow and having a front end being open for holding a suppository and a back end;

a grippable lip formed at said back end of said barrel;

a plunger disposed within said barrel for sliding transversely between an extended position and a withdrawn position, said plunger entering said front end of said cylindrical barrel when in said extended position;

a stop shield mounted in an annularly extended manner about said barrel; and said stop shield threadedly engaged on said barrel in such a manner as to permit longitudinal movement of the stop shield along the barrel only when a rotational force is applied to the stop shield, said stop shield both for preventing over insertion of said front end of said barrel and for maintaining hygiene integrity at said back end of said barrel.

2. The suppository applicator as described in claim 1, wherein said cylindrical barrel at said front end forms a suppository holding chamber.

3. The suppository applicator as described in claim 1, wherein said plunger further comprises:

an elongated plunger shaft having opposite a first end and a second end;

a plunger head mounted perpendicularly across said plunger shaft at said first end, said plunger head fitting engaging within said front end of said barrel; and a plunger handle mounted perpendicularly across said plunger shaft at said second end in a manner aligned with said grippable lip.

4. The suppository applicator as described in claim 1, wherein said barrel, said plunger, and said stop shield are formed of injected molded plastic material.

5. In a suppository applicator having a cylindrical barrel being hollow and having a front end being open for holding a suppository and a back end, and a plunger disposed within said barrel for sliding transversely between an extended position and a withdrawn position, wherein the improvement comprises:

a stop shield mounted in an annularly extended manner about said barrel; and said stop shield threadedly engaged on said barrel in such a manner as to permit longitudinal movement of the stop shield along the barrel only when a rotational force is applied to the stop shield, said stop shield both for preventing over insertion of said front end of said barrel and for maintaining hygiene integrity at said back end of said barrel.

6. In a suppository applicator as described in claim 5, wherein the improvement further comprises:

a grippable lip formed at said back end of said barrel.

7. The suppository applicator as described in claim 5, wherein said barrel, said plunger, and said stop shield are formed of injected molded plastic material.

\* \* \* \* \*